United States Patent [19]

Simons et al.

[11] 4,435,517

[45] Mar. 6, 1984

[54] COBALT HYDROFORMYLATION CATALYSTS

[75] Inventors: Leslie H. Simons; David C. Alexander, both of Austin, Tex.

[73] Assignee: Texaco Inc., White Plains, N.Y.

[21] Appl. No.: 414,194

[22] Filed: Sep. 2, 1982

[51] Int. Cl.³ .......................... B01J 29/14; B01J 29/24
[52] U.S. Cl. ....................................................... 502/74
[58] Field of Search .................................... 252/455 Z

[56] References Cited

U.S. PATENT DOCUMENTS

| | | | |
|---|---|---|---|
| 3,013,984 | 12/1961 | Breck | 252/455 Z |
| 3,013,990 | 12/1961 | Breck et al. | 252/455 Z |
| 3,880,938 | 4/1975 | Massie | 252/455 Z |
| 4,201,728 | 5/1980 | Hughes | 568/454 |

*Primary Examiner*—Carl F. Dees
*Attorney, Agent, or Firm*—Robert A. Kulason; Jack H. Park; Richard A. Morgan

[57] ABSTRACT

This invention relates to a new process for the preparation of aldehydes by the reaction of carbon monoxide and hydrogen with olefins in the presence of hydroformylation catalyst. The invention also relates to a new supported cobalt hydroformylation catalyst and a process for catalyst preparation.

10 Claims, No Drawings

COBALT HYDROFORMYLATION CATALYSTS

BACKGROUND OF THE INVENTION

1. Field of the Invention

It is well known in the art that oxygenated organic compounds may be synthesized from organic compounds containing olefinic linkages by a reaction with carbon monoxide and hydrogen in the presence of a catalyst containing cobalt in an essentially three-stage process. In the first stage, the olefinic material and proper proportions of CO and $H_2$ are reacted in the presence of the catalyst to give a product consisting predominantly of aldehydes containing one more carbon atom than the reacted olefin. The catalyst in the first stage of the process has generally been added in the form of high molecular weight fatty acid salts of the catalytically active metal. These salts are soluble in the liquid olefin feed or in the liquid reaction products and have been supplied to the first stage as hydrocarbon solutions or dissolved in the olefin feed. Also it has been proposed to employ catalyst deposited on a carrier in the form of a slurry and employ the supported cobalt material in the slurry rather than the metal soap. Regardless of the form of catalyst employed, prior investigations have concluded that the active form of the catalyst utilized in the reaction is a metal carbonyl formed by a reversible reaction of the catalyst with the CO and $H_2$ at hydroformylation conditions. This theory is supported by the fact that preformed catalysts, obtained by subjecting the metal salt to hydroformylation conditions prior to introduction of the olefin feed, have shown a marked reduction in induction time, which is the time required to initiate reaction measured from the instant that reaction conditions are first obtained. Regardless of the form of catalyst used, prior art investigators have found that the oxygenated organic mixture obtained from the first stage of the reaction contained, dissolved therein, compounds such as carbonyls and molecular complexes of the metal catalysts. The organic mixture is therefore treated in a second stage to cause removal of soluble metal compounds from the organic material. This treatment is necessary to remove the metal compounds since they separate out on the catalysts used and plug transfer lines and heat exchangers. This treating has been carried out, for example, by the use of acids or heat. The catalyst-free material is then generally hydrogenated to the corresponding alcohols or it may be oxidized to the corresponding acids.

2. Prior Art: Catalyst Preparation

Catalysts of the present invention are made by the metal vaporization synthesis technique (J. R. Blackborow and D. Young, "Metal Vapour Synthesis in Organometallic Chemistry", Springer-Verlag, New York 1979). By this technique, metal is vaporized in a furnace under pressure of $10^{-3}$ to $10^{-8}$ Torr or less and at temperatures which vary according to the metal, usually from 800° C. to 2500° C. Furnaces used for the metal vaporization synthesis technique include electron beam guns, resistance heated furnaces, laser beam heating, hot filaments and electric arcs. Electron beam guns and resistance heated furnaces are convenient and preferred methods for catalyst preparation.

3. Prior Art: Hydroformylation

Hydroformylation refers to the reaction of an olefin with hydrogen and carbon monoxide in the presence of a cobalt catalyst to produce aldehydes containing one carbon atom more than that of the olefin in the feed. The reaction is carried out by bringing the olefin and slurry of cobalt catalyst in contact with carbon monoxide and hydrogen. Commercially, the carbon monoxide and hydrogen are supplied by synthesis gas, with the ratio of $H_2:CO$ usually being 1:1. Although equal molar quantities of synthesis gas and olefin are consumed, normally synthesis gas is supplied in excess. This reaction is represented generally, by the hydroformylation of propylene to give n-butyraldehyde and i-butyraldehyde in the ratio of 3:2.

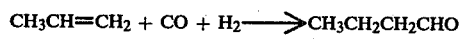

and

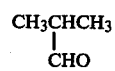

U.S. Pat. No. 3,352,924 describes cobalt substituted zeolite catalysts which require a synthesis gas pressure of about 2500 psig for hydroformylation activity. P. Centola et al., *Chim. Ind.* (Milan), 54, 775 (1972) describes cobalt exchanged zeolites for hydroformylation of propylene at pressures of 2000 to 4500 psig.

In commercial practice, the process involves a second step in which aldehydes are reduced with hydrogen to primary alcohols. The liquid oxygenated product obtained from hydroformylation in the presence of the catalyst of this invention may be fed directly to a hydrogenation zone where it is hydrogenated under conventional conditions to obtain substantial yields of primary alcohols. Conventional hydrogenation conditions typically include pressures in the range of 2,000 to 4,000 psig and temperatures in the range of 300° F. to 550° F. Hydrogenation conditions will vary with the choice of catalyst with nickel, molybdenum sulfide or the like representing conventional choices. Typical hydrogenation conditions may be found in U.S. Pat. No. 2,771,493.

SUMMARY OF THE INVENTION

This invention concerns a novel process for the hydroformylation of olefinic compounds. Another objective of this invention is to provide a novel catalyst which results in conversions of the olefinic starting materials to desirable aldehyde products at conditions that are milder than have heretofore been known in the art. A further objective of the invention is to provide a process for the preparation of catalyst.

The present invention relates to a process for the hydroformylation of olefinic compounds comprising reacting said olefinic compounds with carbon monoxide and hydrogen in the presence of a porous catalyst support which has from about 0.1 wt. % to about 5 wt. % of metallic cobalt(0) deposited thereon.

DETAILED DESCRIPTION OF THE INVENTION

The hydroformylation process of this invention may be carried out using known feedstocks for such processes and provides an attractive method, due to its relatively mild processing conditions, for preparing valuable primary alcohols which are intermediate for plasticizers, detergents and solvents.

Catalyst Preparation

The process for the preparation of hydroformylation catalyst comprises:

(a) vaporizing metallic cobalt(0);

(b) cocondensing the metallic cobalt(0) with a solvent to form a metallic cobalt(0)-solvent matrix;

(c) melting the metallic cobalt(0)-solvent matrix and thereby forming a metallic cobalt(0)-solvent slurry;

(d) absorbing the metallic cobalt(0)-solvent slurry on dry, oxygen free, porous catalyst support;

(e) removing the solvent and thereby producing a catalyst which has from about 0.1 wt % to about 5 wt % and preferably 0.6 wt % to 0.9 wt % of metallic cobalt(0) deposited thereon.

Catalysts of the present invention are made by the metal vaporization synthesis technique. By this technique, metallic cobalt(0) is vaporized in a furnace under pressure of about $10^{-3}$ to about $10^{-6}$ Torr or less and at a temperature of about 1300° C. to about 1500° C. The vaporized metallic cobalt(0) proceeds by collision free path from the furnace to a condensation site which for purposes of this invention is the inner wall of the reaction vessel. At the condensation site, the metal is condensed with a hydrocarbon solvent such as aromatics, ethers, alkanes and olefins at a convenient condensation temperature such as about $-78°$ C. for solid carbon dioxide to about $-196°$ C. for liquid nitrogen. Aromatic solvents include benzene, toluene, xylene and the like. Alkane solvents include hexanes, heptanes, octanes, nonanes, decanes, cyclohexane and the like. Olefin solvents include all of the olefins suitable as substrates.

A preferred method of maintaining the temperature because of convenience is liquid nitrogen bath. Condensation temperature is not critical so long as the solvent and metallic cobalt(0) cocondense. The temperature of solid carbon dioxide and liquid nitrogen are not considered limitative but are presented merely to reveal techniques which have proven successful in the laboratory. The condensed metallic cobalt(0)-solvent matrix is melted to form a metallic cobalt(0)-solvent slurry and is absorbed on dried, oxygen free, porous catalyst support present in the reaction vessel. Finally, hydrocarbon solvent is removed under vacuum as the reaction vessel warms, typically to room temperature 25° C. The result of this process is the hydroformylation catalyst of the present invention which is metallic cobalt(0) on dried porous catalyst support. The quantity of metal on support can be determined by atomic absorption analysis.

A preferred class of porous catalyst supports is a zeolite. One preferred zeolite is an alumino-silicate zeolite. These alumino-silicate zeolites have an effective pore diameter within the range of 3 to 15 angstroms; with the large pore, e.g. 6 to 15 angstroms, types being preferred. However, exchanged A-type alumino-silicate zeolites which, in the calcium form, have pore diameters of only 5 angstroms (alumina to silica ratios in the zeolite of about 1.8 to 2.3) may also be used, as well as Mordenite type zeolites.

As employed in the present specification, the term "large pore zeolites" refers to metallic alumino-silicate zeolites characterized by their highly ordered crystalline structure and having pores of nearly uniform dimensions in the range of about 6 to 15 angstroms. These crystalline zeolites have an alumino-silicate anionic cage structure in which the alumina and silica tetrahedra are intimately connected to each other. Metal cations or hydrogen are distributed throughout the structure to maintain electrical neutrality. The highly ordered dispersion of the silica and alumina tetrahedra makes for a large number of active sites, and the uniform pore openings of 6 to 15 angstrom units allow for easy ingress of various hydrocarbon feed types as well as egress of the reaction products which may be formed by contact with the zeolites.

Such large pore zeolites are sometimes referred to as "Type 13" molecular sieves. A naturally occurring example thereof is the mineral faujasite. Synthetically produced alumino-silicates have been termed in the industry "13X" and "13Y" molecular sieves.

The metal cation is preferably an alkali metal such as sodium or potassium or an alkaline earth metal such as calcium. Normally, it is sodium. The smaller pore zeolites differ principally in having a silica/alumina ratio of 1.8 to 2.3.

Experience has shown that a 50 fold excess of organic solvent to metallic cobalt(0) is required to deposit 0.1 wt. % to 5 wt. % of metal on porous catalyst support. Final analysis of metal on catalyst is performed by atomic absorption spectroscopy.

Hydroformylation Catalyst

Hydroformylation catalyst of the present invention is prepared by:

(a) vaporizing metallic cobalt(0);

(b) cocondensing the metallic cobalt(0) with a solvent to form a metallic cobalt(0)-solvent matrix;

(c) melting the metallic cobalt(0)-solvent matrix and thereby forming a metallic cobalt(0)-solvent slurry;

(d) absorbing the metallic cobalt(0)-solvent slurry on dry, oxygen free porous catalyst support; (e) removing the solvent and thereby producing a catalyst which has from about 0.1 wt % to about 5 wt % and preferably 0.6 wt % to 0.9 wt % of metallic cobalt(0) deposited thereon.

Metallic cobalt(0) is vaporized in a furnace under pressure of about $10^{-3}$ to about $10^{-6}$ Torr and temperature of about 1300° C. to about 1500° C. A typical porous catalyst support is a zeolite. Preferred porous catalyst supports are metallic alumino-silicate zeolites having pore diameters in the range of about 3 anstroms to about 15 angstroms and preferably about 6 angstroms to about 15 angstroms.

Catalyst prepared by this method contains metallic cobalt which is inherently in the zero oxidation state. Preparation of hydroformylation catalyst by this method was previously unknown. The instant catalyst demonstrates superior characteristics such as catalyst activity. Cobalt catalyst preparation methods known in the art typically exchange a cobalt salt with sodium atoms in the zeolite structure. A subsequent reduction step at 2000 psig renders cobalt to the zero oxdation state but with the cost of a reduction in activity. No additional processing step is required with the present catalyst because cobalt on the catalyst produced is inherently in the zero oxidation state.

The mechanism for the retention of metallic cobalt(0) on the zeolite is not known with certainty. It is thought that surface hydroxyl groups bond the metal to the zeolite surface. Whatever the mechanism, the activity of the instant catalyst is greatly improved over the prior art. Because of the improved activity, hydroformylation pressures of 900 psig or lower are permitted where pressures of 2500 psig or higher are typical in the prior art.

The Hydroformylation Process

The amount of catalyst utilized in the process of the present invention when using a slurry-type operation may vary from 1 to 50 wt. percent based on olefin feed and preferably 3 to 30 wt. percent. Amenable to the reaction are long and short-chain olefinic compounds, depending upon the type of alcohols desired. Not only olefins, but most organic compounds possessing at least one non-aromatic carbon-carbon double bond may be reacted by this method. Thus, straight and branched-chain olefins and diolefins, such as propylene, butylene, pentene, hexene, heptene, butadiene, pentadiene, styrene, olefin polymers, such as di- and tri-isobutylene and hexene and heptene dimers polypropylene, olefinic fractions from the hydrocarbon synthesis process, thermal or catalytic cracking operations, and other sources of hydrocarbon fractions containing olefins, may be used as starting material, depending upon the nature of the final product desired.

The ratio of hydrogen to carbon monoxide is not critical. Synthesis gas mixtures wherein the $H_2/CO$ mole ratio ranges from 1/5 to 5/1 are suitable. Preferably, synthesis gas mixtures containing about 1/1 to about 2/1 mole ratio of hydrogen to carbon monoxide are employed. The ratio of synthesis gas to olefin feed is also not critical and in general may be maintained between 2,500 and 15,000 standard cubic feet of hydrogen and carbon monoxide per barrel of olefin feed. Pressures in the range 100 psig to 1,500 psig and temperatures of 100° C. to 250° C. are generally satisfactory. Pressures of 500 psig to 900 psig and temperatures of 150° C. to 190° C. are preferred. It should be noted that these conditions are considered mild with 2500 psig and higher considered heretofore typical (U.S. Pat. No. 3,352,924).

In the commercial application of the process of the present invention, carbon dioxide and sulfur compounds, such as hydrogen sulfide or carbonyl sulfide, must be removed from the synthesis gas. Carbon dioxide is an undesirable diluent. Sulfur compounds do not adversely affect the hydroformylation process but interfere with the hydrogenation of aldehydes to alcohols.

Olefins ranging in carbon number from ethylene to hexadecene have been found suitable for hydroformylation. Mixtures of olefins react as readily as pure compounds, and the presence of saturated hydrocarbons does not interfere with the reactions. Linear olefins containing from 3 to 16 carbon atoms and containing a terminal double bond are preferred because they are suitably reactive and may be synthesized into linear alcohols which are desired products. In the Example is shown propylene and 1-octene as reaction feed. Internal olefins also react suitably in the present invention with internal octenes being demonstrated in the Example.

The porous catalyst support of this process is preferably a zeolite and most preferably a metallic aluminosilicate zeolite having pore diameters in the range of about 3 angstroms to about 15 angstroms and most preferably about 6 angstroms to about 15 angstroms.

This invention is more fully illustrated by the following Example:

EXAMPLE I

A. Catalyst Preparation

The apparatus used in the catalyst preparation consisted of a high vacuum system and a large, flat bottom, heavy-walled reaction vessel fitted with a top containing an electrically heated metal sample basket and means for evacuating the vessel. Attached to the reaction vessel was a ligand vessel from which a ligand or solvent could be distilled into the reaction vessel.

A 50.00 gram sample of Linde 5A zeolite molecular sieve (1/16 inch extrudate) was placed in the reaction vessel with an inert polymer coated stirring bar. The metal sample basket was charged with 1.027 grams (17.4 mg-atoms) of 99.8% 50 mesh cobalt powder. Dried reagent grade toluene (120 ml.) was added to the ligand vessel. The reaction vessel was evacuated to $3 \times 10^{-6}$ Torr and left overnight.

The reaction vessel was cooled in liquid nitrogen and mechanically rotated while toluene was distilled in, which produced a frozen toluene-zeolite coating on the reaction vessel wall. Next, the sample basket was electrically heated to vaporize the cobalt metal. The vaporized cobalt metal condensed onto the frozen toluene-zeolite coating. The cobalt vaporization-condensation step took two hours to accomplish. The liquid nitrogen bath was then removed causing the toluene to melt. The result was a black suspension which was stirred for several hours. Vacuum was broken with argon and the suspension was left at room temperature overnight under argon atmosphere.

Toluene in the vessel was removed by vacuum distillation into a liquid nitrogen cooled trap, leaving the dry, black zeolite catalyst. The catalyst was maintained under argon atmosphere and was found to contain 0.72 wt % cobalt by atomic absorption spectroscopy.

B. Hydroformylation Procedure

The reaction listed in Table 1 were all carried out in a 300 ml., stainless steel autoclave. The olefin or solvent was charged to the autoclave, then the catalyst of the present invention was added and the system was purged with argon for 20 to 30 minutes. The autoclave was then sealed and flushed with $CO/H_2$ gas (1:2 mole ratio) by two pressurization-depressurization cycles.

In Synthesis 5469-8 for example, propylene was added to the autoclave at this point. The system was then pressured to 500 psig and heated to the "reaction temperature" (170° C.) which resulted in a pressure increase to the "initial pressure" (750 psig), both listed in Table I.

After 16 hours the reactor was cooled and the liquid was withdrawn. Gas chromatographic analyses are shown in Table I. Analysis of the solution for cobalt by atomic absorption spectroscopy shows that very little metal was present in solution.

The principle of this invention and the best mode contemplated for applying he principle have been described. It is to be understood that the foregoing is illustrative only and that other means and techniques can be employed without departing from the true scope of the invention defined in the following claims:

TABLE I

| | Zeolite Support | Co present (mg-atoms) | Initial Press. 2:1 $H_2/CO$ (psig) | Reaction Temp. (°C.) | Olefin | Conversion mmol olefin/ mg.atom Co. | % octene remaining | % $C_9$ aldehydes | % C alcohols | Co in product Solution (ppm) |
|---|---|---|---|---|---|---|---|---|---|---|
| Synthesis 5469-25 | 5A$^c$ | 0.15 | 700 | 180 | internal octenes | 86 | 81 | 7.3 | 0.8 | |

TABLE I-continued

| | Zeolite Support | Co present (mg-atoms) | Initial Press. 2:1 H$_2$/CO (psig) | Reaction Temp. (°C.) | Olefin | Conversion mmol olefin/ mg.atom Co. | % octene remaining | % C$_9$ alde- hydes | % C alcohols | Co in product Solution (ppm) |
|---|---|---|---|---|---|---|---|---|---|---|
| 5501-42 | 13X$^d$ | 0.21 | 820 | 170 | 1-octene | 106 | 79 | 9.2 | 4.6 | 10 |
| 5523-19 | 13X$^d$ | 0.17 | 750 | 178 | internal octenes | 75 | 89 | 4.7 | 3.6 | |
| 5469-10 | 5A$^c$ | 0.18 | 700$^a$ | 170 | 1-octene | 97 | 77 | 10.2 | 0.8 | 122 |
| 5469-8 | 5A$^c$ | 0.14 | 750 | 170 | propylene$^b$ | (toluene 200 92 | (Butyraldehydes) solvent) 7 | | | 74 |
| Comparative Synthesis | | | | | | | | | | |
| 5568-27 | NaY$^e$ | 0.11 | 800 | 155 | 1-octene | — | 97 | — | — | |

$^a$1:1 H$_2$/CO
$^b$Toluene Solvent
$^c$5 Angstrom alumino-silicate
$^d$10 Angstrom alumino-silicate
$^e$8 Angstrom alumino-silicate
The cobalt/5A and cobalt/13X catalysts were prepared of cobalt atom/toluene slurry onto support and contained 0.72 wt. % (5A) and 0.88 wt. % (13X) Co. The cobalt/NaY catalyst was prepared by exchange with a solution of cobalt nitrate and contained 1.77 wt. % Co.
Reactions were all conducted in a 300 ml stirred autoclave with 25 ml (159 mmol) octene(s). Analyses were by gas chromatography.

What is claimed is:

1. A hydroformylation catalyst which is prepared by:
   (a) vaporizing metallic cobalt(0);
   (b) cocondensing the metallic cobalt(0) with a solvent to form a metallic cobalt(0)-solvent matrix;
   (c) melting the metallic cobalt(0) and solvent matrix and thereby forming a metallic cobalt(0)-solvent slurry;
   (d) absorbing the metallic cobalt(0)-solvent slurry on dry, oxygen free porous catalyst support;
   (e) removing the solvent and thereby producing a catalyst which has from about 0.1 wt % to about 5 wt % of metallic cobalt(0) deposited thereon.

2. The hydroformylation catalyst of claim 1 wherein step (a) metallic cobalt(0) is vaporized at a pressure of about $10^{-3}$ to about $10^{-6}$ Torr and temperature of about 1300° C. to about 1500° C.

3. The hydroformylation catalyst of claim 1 wherein the solvent is toluene.

4. The hydroformylation catalyst of claim 1 wherein the catalyst has from about 0.6 wt. % to about 0.9 wt. % of metallic cobalt(0) deposited thereon.

5. A process for the preparation of hydroformylation catalyst containing metallic cobalt(0) which comprises:
   (a) vaporizing metallic cobalt(0);
   (b) cocondensing the metallic cobalt(0) with a solvent to form a metallic cobalt(0)-solvent matrix;
   (c) melting the metallic cobalt(0) and solvent matrix and thereby forming a metallic cobalt(0)-solvent slurry;
   (d) absorbing the metallic cobalt(0)-solvent slurry on dry, oxygen-free porous catalyst support,
   (e) removing the solvent and thereby producing a catalyst which has from about 0.1 wt % to about 5 wt % of metallic cobalt(0) deposited thereon.

6. The process of claim 5 wherein step (a) metallic cobalt(0) is vaporized at a pressure of about $10^{-3}$ to about $10^{-6}$ Torr and temperature of about 1300° C. to about 1500° C.

7. The process of claim 5 wherein the solvent is toluene.

8. The process of claim 5 wherein the porous catalyst support is a metallic alumino-silicate zeolite having pore diameters in the range of about 3 angstroms to about 15 angstroms.

9. The process of claim 5 wherein the porous catalyst support is a metallic alumino-silicate zeolite having pore diameters in the range of about 6 to about 15 angstroms.

10. The process of claim 5 wherein the catalyst has from about 0.6 wt % to about 0.9 wt % of metallic cobalt(0) deposited thereon.